US006371958B1

United States Patent
Overaker

(10) Patent No.: US 6,371,958 B1
(45) Date of Patent: Apr. 16, 2002

(54) SCAFFOLD FIXATION DEVICE FOR USE IN ARTICULAR CARTILAGE REPAIR

(75) Inventor: David W. Overaker, Annandale, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/517,602

(22) Filed: Mar. 2, 2000

(51) Int. Cl.$^7$ ................................................ A61B 17/84
(52) U.S. Cl. ........................................ 606/72; 606/151
(58) Field of Search ............................ 606/53, 60, 72, 606/73, 75, 151, 232; 623/13.11, 13.12, 14.12

(56) References Cited

U.S. PATENT DOCUMENTS

| | | |
|---|---|---|
| 5,067,964 A | 11/1991 | Richmond et al. |
| 5,306,311 A | 4/1994 | Stone et al. |
| 5,624,463 A | 4/1997 | Stone et al. |
| 5,632,745 A | 5/1997 | Schwartz |
| 5,713,374 A | 2/1998 | Pachence et al. |
| 5,749,874 A | 5/1998 | Schwartz |
| 5,769,899 A | 6/1998 | Schwartz et al. |
| 6,036,694 A | * 3/2000 | Goble et al. .................. 606/72 |
| 6,152,928 A | * 11/2000 | Wenstrom, Jr. ............... 606/72 |

OTHER PUBLICATIONS

"Cartilage Induction by Controlled Mechanicl Stiumulation In Vivo"; Magnus Tagil et al.; Journal of Orthopaedic Research; 17:200–206, 1999.

"Chondrocyte Cells Respond Mechanically to Compressive Loads"; P.M. Freeman et al.; Journal of Orthopaedic Research; 12:311–320, 1994.

"The Effects of Hydrostatic Pressure on Matrix Synthesis in Articular Cartilage"; A. C. Hall et al.; Journal of Orthopaedic Research; 9:1–10, 1991.

* cited by examiner

Primary Examiner—David O. Reip

(57) ABSTRACT

The present invention provides a scaffold fixation device for fastening an articular cartilage scaffold to underlying bone, which device provides controlled loading of the cartilage scaffold.

5 Claims, 14 Drawing Sheets

SCAFFOLD FIXATION DEVICE FOR USE IN ARTICULAR CARTILAGE REPAIR

FIELD OF THE INVENTION

The present invention relates to scaffold fixation devices useful in articular cartilage repair and more specifically to a device for fastening an articular cartilage scaffold to underlying bone.

BACKGROUND OF THE INVENTION

Tissue engineering is defined as the application of engineering disciplines to either maintain existing tissue structures or to enable new tissue growth. This engineering approach generally includes the delivery of a tissue scaffold that serves as an architectural support onto which cells may attach, proliferate, and synthesize new tissue to repair a wound or defect. Cartilage tissue scaffolds have high open-celled porosity to allow cell migration throughout the scaffold and also to allow important nutrient-bearing fluids to flow through the scaffold to maintain the health of the cells.

Articular cartilage is a tissue that covers the articulating surfaces between bones in the joints. Articular cartilage consists of two principal phases: a solid matrix and an interstitial fluid phase. The matrix, which gives cartilage its stiffness and strength, is produced and maintained by chondrocytes. Many studies have indicated that load has an important influence on matrix synthesis and on the composition of articular cartilage. Published studies have described the effect of mechanical loading on cell activity and matrix synthesis in cartilage: Hall, Urban, and Gehl, "The Effects of Hydrostatic Pressure on Matrix Synthesis in Articular Cartilage", *Journal of Orthopaedic Research,* Vol. 9, pp. 1–10, 1991; Freeman, Natarajan, Kimura, and Andriacchi, "Chondrocyte Cells Respond Mechanically to Compressive Loads", *Journal of Orthopaedic Research,* Vol. 12, pp. 311–320, 1994; Tagil and Aspenberg, "Cartilage Induction by Controlled Mechanical Stimulation In Vivo, *Journal of Orthopaedic Research,* Vol. 17, pp. 200–204, 1999 and; Carver and Heath, "Semi-continuous Perfusion System for Delivering Intermittent Physiological Pressure to Regenerating Cartilage", *Tissue Engineering,* Vol. 5, pp. 1–11, 1999.

Synthetic absorbable biocompatible polymers are well known in the art. Such polymers typically are used to manufacture medical devices which are implanted in body tissue and absorb over time. Synthetic absorbable biocompatible aliphatic polyesters include homopolymers, copolymers (random, block, segmented and graft) of monomers such as glycolic acid, glycolide, lactic acid, lactide (d, l, meso and mixtures thereof), caprolactone, trimethylene carbonate and p-dioxanone. Numerous U.S. Pat. Nos. describe these polymers, including 5,431,679; 5,403,347; 5,314,989; 5,431,679; 5,403,347; and 5,502,159. Devices made of an absorbable material have the advantage that they are absorbed by the body after healing has occurred.

U.S. Pat. No. 5,067,964 describes an articular cartilage repair piece which includes a backing layer of non-woven, felted fibrous material which is either uncoated or covered by a coating of tough, pliable material. A number of means are disclosed for fastening the repair piece to the underlying bone. U.S. Pat. Nos. 5,306,311 and 5,624,463 describe a prosthetic, resorbable articular cartilage and methods of its fabrication and insertion. U.S. Pat. No. 5,713,374 describes an attachment method to hold a biomaterial in place until healing occurs. U.S. Pat. Nos. 5,632,745 and 5,749,874 and 5,769,899 describe a bioabsorbable cartilage repair system.

High porosity is a critical design criterion in engineering of tissue scaffolds. Since a very porous tissue scaffold will have low stiffness and strength, a device is needed that will protect the scaffold from high joint loads. The same device needs to provide controlled mechanical stimulation of the cells within the scaffold to increase cell activity and matrix synthesis to produce new cartilage.

Accordingly, it would be advantageous to provide a scaffold fixation device which allows limited loading of the scaffold effective to stimulate tissue regeneration within the scaffold, while also providing protection of the scaffold from excessive loading that may damage the repairing tissue.

SUMMARY OF THE INVENTION

The present invention is directed to scaffold fixation devices comprising means for anchoring the device to bone, a load support comprising an upper surface, and means for providing deformation of the device.

DETAILED DESCRIPTION OF THE INVENTION

Figure 1:
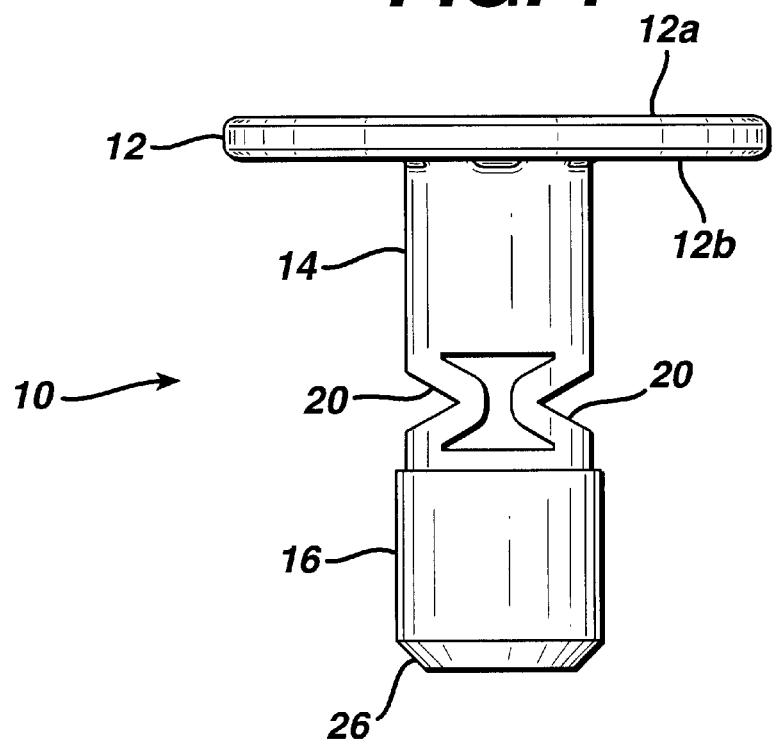
FIG. 1 is a side elevation view of a one-piece of the present invention.

The present invention provides a device for fastening an articular cartilage scaffold to underlying bone. The device comprises means for providing deformation of the device.

The deformation is selected so as to provide a particular controlled load on the cartilage scaffold. The controlled load is sufficient to stimulate cell growth and matrix synthesis, while at the same time not excessive so as to cause substantial cell and tissue damage. As used herein, "deformation" means linear displacement of the upper surface of the load support relative to the original position of the upper surface of the load support. The amount of deformation required in a particular situation is determined in part by such factors as the properties of materials selected for the device and the cartilage scaffold, respectively, e.g. strength, stiffness, etc. and the amount of load effective to stimulate cell growth and matrix synthesis without substantially damaging the cells or tissue.

One device of the invention comprises a single integral part, comprising a load support having an upper surface, means for providing controlled deformation of the device and means for anchoring the device to bone. The load support resides above the cartilage scaffold, is flush with the neighboring healthy cartilage and is in direct contact with the opposing joint surface. The anchoring means may comprise a fixation post that protrudes from the load support, through the cartilage scaffold, and into the underlying bone, thereby anchoring the device, and thus the cartilage scaffold, within the cartilage defect space. Load applied by the opposing joint surface is transmitted through the load support to the underlying scaffold and/or bone, depending on the amount of load transmitted.

The anchor means may comprise means for providing controlled deformation of the device. Such means permits selected linear displacement of the upper surface of the load support, relative to its original position, in response to the load applied by the opposing joint surface. When the load is sufficiently low, so as not to cause substantial damage to the cartilage scaffold, cells or tissue, the device may deform, such that the load may be borne mostly by the cartilage scaffold. In this way, a minimum load may be applied to the cartilage scaffold to stimulate cell growth and matrix synthesis. When the load becomes excessive, such that damage to the cartilage scaffold, or to cells or tissue may occur, the a device is prevented from deforming further and the excessive load is transferred directly to the underlying bone via the fixation device, thereby shielding the scaffold from excessive load.

One means of providing controlled deformation comprises flexible structural members that fold, or collapse, or otherwise deform in response to load applied to the load support, thus providing limited mechanical response, i.e. stiffness, to the load, thereby transferring a substantial portion of the load to the cartilage scaffold. Once maximum deformation is achieved, e.g. when the collapsing member can collapse no further or meets a constraint, the mechanical response of the device becomes greater and the device bears a greater to a substantial portion of the load, thereby preventing damage to the cells or scaffold.

Other devices of the invention comprise an assembly of two parts, between which the cartilage scaffold resides. The two parts are pressed together to engage mechanical fasteners that, once fully engaged, prevent the parts from being separated. The connected parts are free to move with respect to each other, i.e. the device is free to deform, through a controlled deformation distance (CDD) between the assembled parts. The CDD is effective to provide a load on the cartilage scaffold effective to stimulate cell activity and matrix synthesis without causing substantial damage to the scaffold or cells and healing tissue. When the load is sufficiently low so as not to cause substantial damage to the scaffold and/or cells, deformation, i.e. relative travel between the two parts, is less than the CDD and the applied load is borne substantially by the scaffold. When the load becomes excessive, the distance between the two parts is closed and the two parts are in contact, thus preventing additional deformation. A substantial portion of the load then is transferred directly to the underlying bone via the device, thus protecting the scaffold from excessive load.

Figure 2:
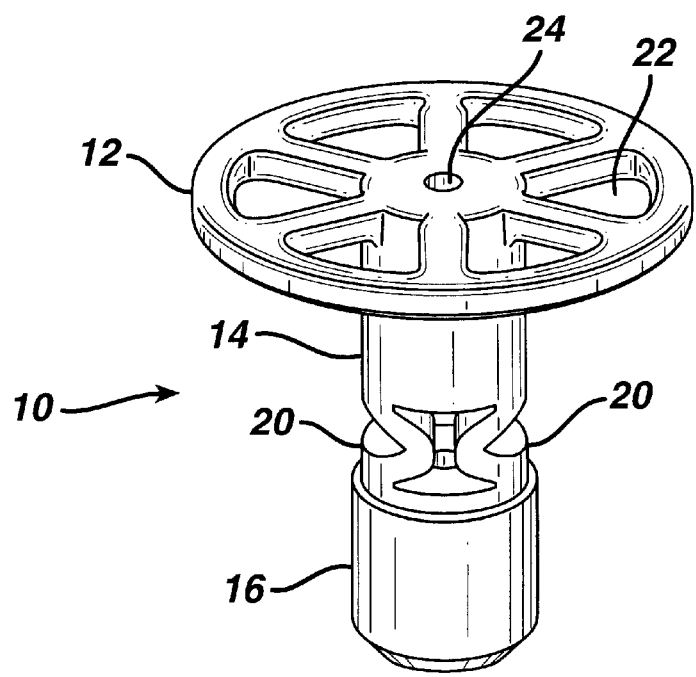
FIG. 2 is a perspective view of the device of FIG. 1.
Figure 3:
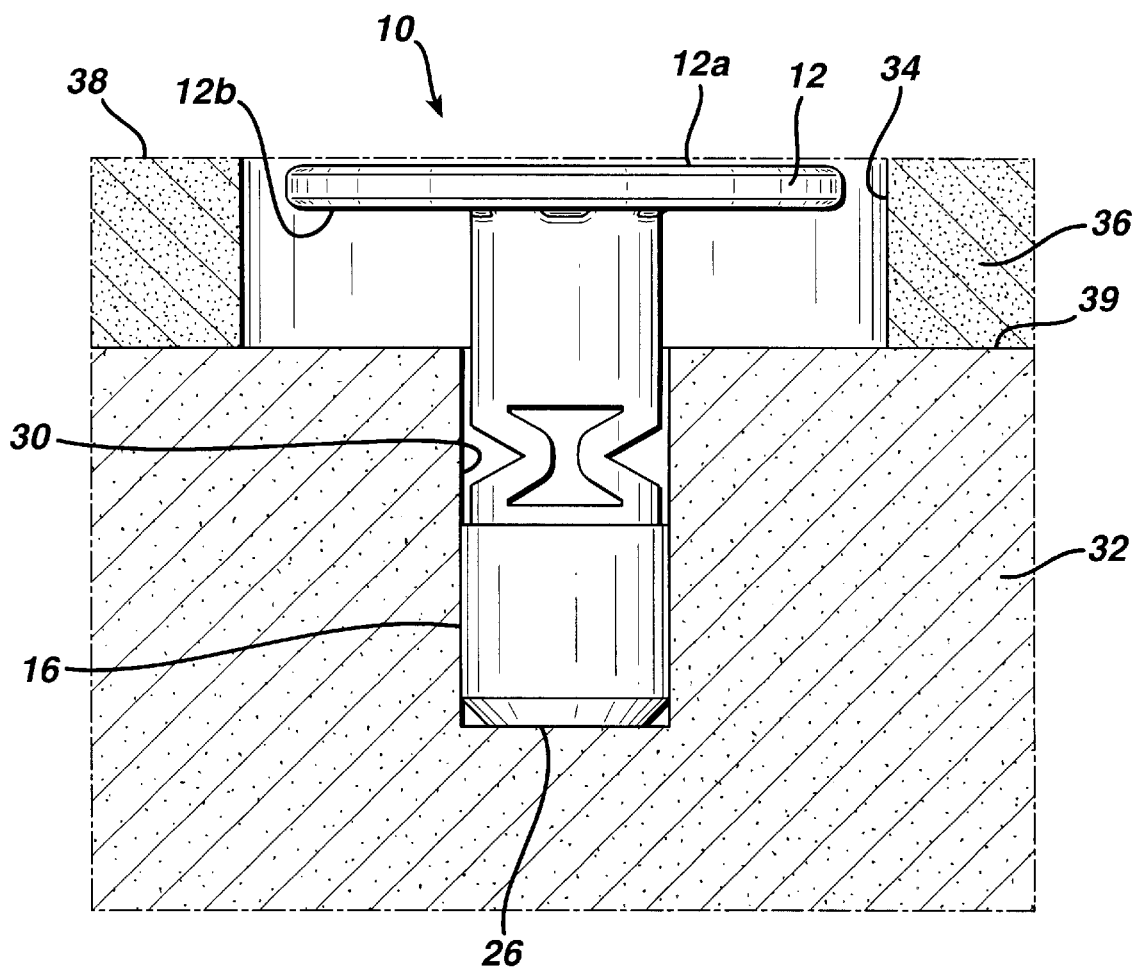
FIG. 3 is a side elevation view of the device of FIG. 1.

One embodiment of the present invention is shown in FIGS. 1 through 3. FIG. 1 shows a side elevation view of scaffold fixation device 10, comprising load support 12 having upper surface 12a and lower surface 12b, fixation post 14, anchoring section 16 and flexible members 20. Flexible members 20 are designed such that the mechanical response is very nonlinear, having low stiffness under low load or displacement and much higher stiffness under high load or displacement. Preferably, the initial compressive stiffness of the flexible members is less than the compressive stiffness of the scaffold. A dramatic increase in stiffness occurs when the displacement of load support 12 is such that flexible members 20 fold upon themselves or are constrained from further bending. Load applied by the opposing joint surface is transmitted through load support 12 and is shared by fixation post 14 and the scaffold. In the low load regime in which flexible members 20 may bend, the scaffold bears the majority of the total applied load. Once the applied load becomes excessive, flexible members 20 fold together or are constrained from further bending and the device will become stiffer, thus transferring excess load directly to the underlying bone via the device. The scaffold thereafter will bear a much lower percentage of the total applied load.

FIG. 2 shows a perspective view of scaffold fixation device 10 showing perforations 22 in load support 12 and guide wire channel 24 traveling longitudinally through the device along the axis of fixation post 14. Perforations 22 allow fluid to flow to and from the scaffold and are not limited to the shape or arrangement show in the figures.

FIG. 3 shows a side elevation view of the surgical placement of scaffold fixation device 10. Bone hole 30 is drilled in bone tissue 32 to a diameter such that an interference fit is made between bone hole 30 and anchoring section 16. Cartilage hole 34 is drilled in cartilage tissue 36 to a diameter at least as large as the outermost diameter of load support 12. The depth of bone hole 30 is drilled such that when fixation post 14 is inserted completely into the hole, upper surface 12a of load support 12 preferably lies in alignment with or slightly below upper cartilage surface 38 of adjacent cartilage tissue 36 when no vertical load is applied to the device. The scaffold would reside within the space available between lower surface 12b of load support 12 and top surface 39 of bone tissue 32 and would fill the diameter of cartilage hole 34. Anchoring section 16 also may include ribs, serrations, or other surface roughness or engagement features that improve the attachment of anchoring section 16 to the surrounding bone hole 30 and substantially prevent rotation of device 10 and the scaffold. Anchoring section 16 also may include chamfer 26, which aids in guiding the fixation post into bone hole 30. A surgical guide wire may be passed through guide wire channel 24 during surgery to align scaffold fixation device 10 with the cartilage repair site.

Figure 4:
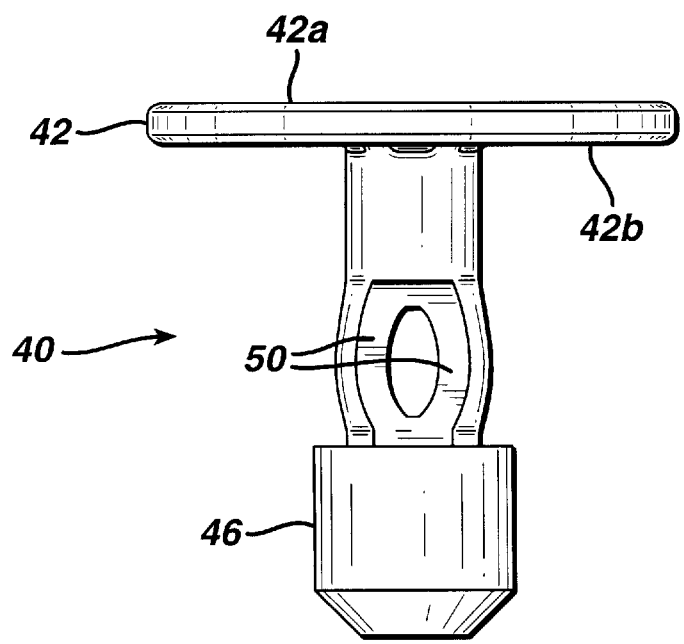
FIG. 4 is a side elevation view of a device of the present invention.
Figure 5:
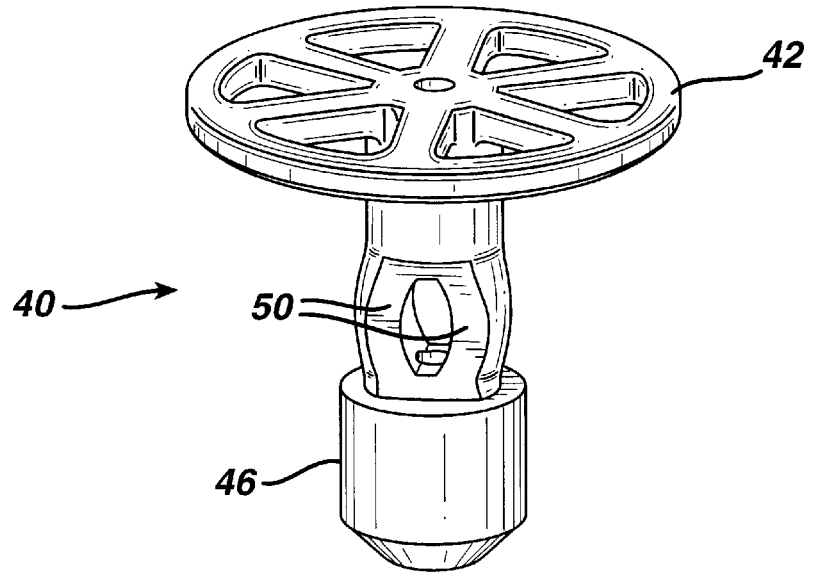
FIG. 5 is a perspective view of the device of FIG. 4.
Figure 6:
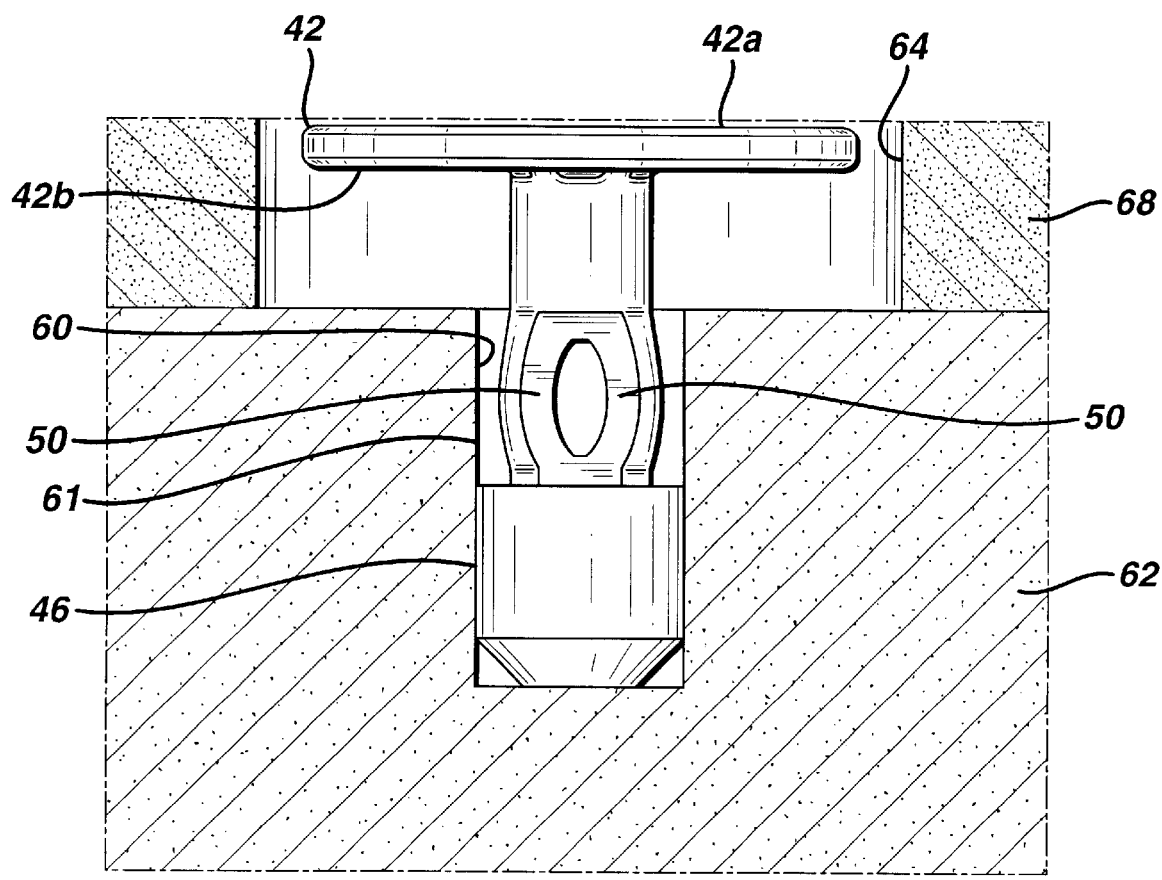
FIG. 6 is a side elevation view of the device of FIG. 4 as deployed in bone.

FIGS. 4, 5 and 6 show a scaffold fixation device of the present invention comprising load support 42 having upper surface 42a and lower surface 42b, fixation post 44, anchoring section 46 and flexible members 50. Flexible members 50 are oriented such that they will bend outwards when a compressive load is applied to load support 42. The stiffness of the device will be relatively low until flexible members 50 contact lateral surface 61 of bone hole 60, at which point the stiffness of the device will increase dramatically, since flexible members 50 are thereafter constrained from further bending outwards. Also shown in FIG. 6 are cartilage hole 64, cartilage tissue 68 and bone tissue 62.

Figure 7:
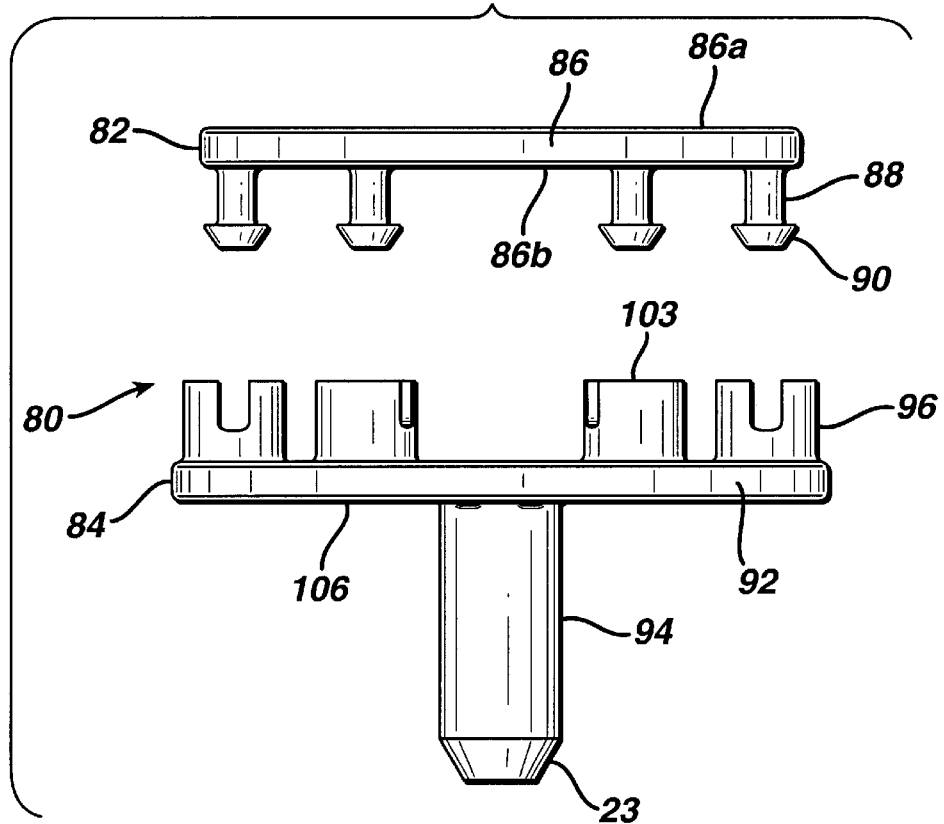
FIG. 7 is a side elevation view of a two-piece device of the present invention.
Figure 8:
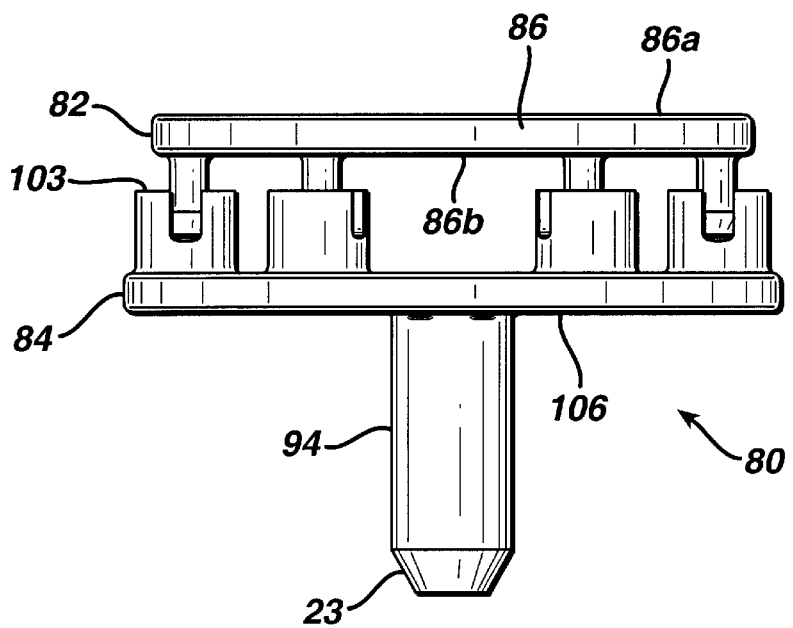
FIG. 8 is a side elevation view of the device of FIG. 7 after connection of the pieces.

A scaffold fixation device of the present invention is shown in FIGS. 7 through 13. FIG. 7 shows a side view of the unassembled scaffold fixation device 80 comprising upper component 82 and base component 84. Upper component 82 comprises load support 86 having upper surface 86a and lower surface 86b and posts 88 which protrude downward from load support 86 near its outer perimeter. Each post 88 contains ledge 90 with outer diameter larger than that of post 88. Base component 84 comprises base platform 92, fixation post 94, and post guides 96 which protrude upward from base platform 92 near its outer perimeter and in axial alignment with posts 88 of upper component 82. FIG. 8 shows a side view of scaffold fixation device 80 after connection of upper component 82 and base component 84.

Figure 9:
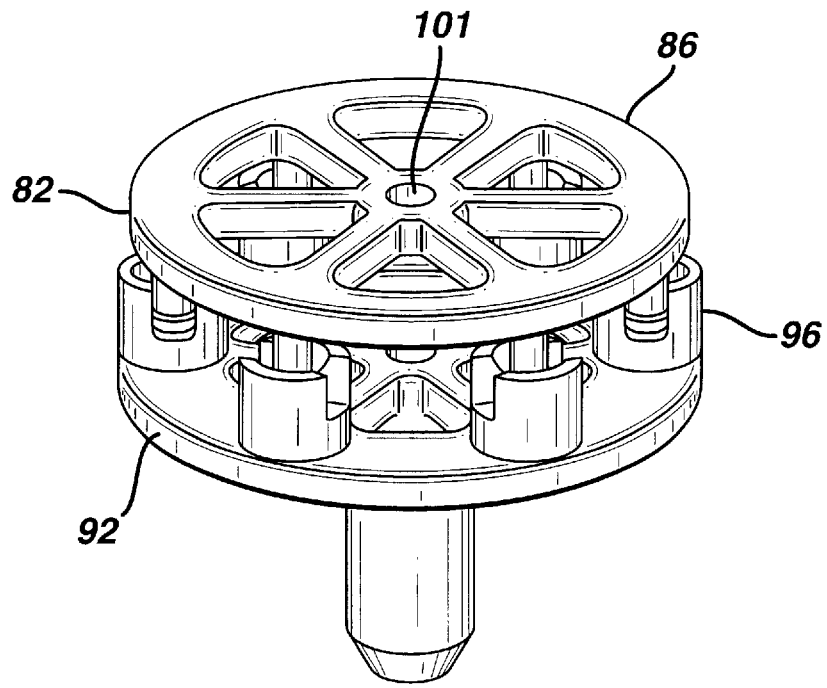
FIG. 9 is a perspective view of the device of FIG. 8.
Figure 10:
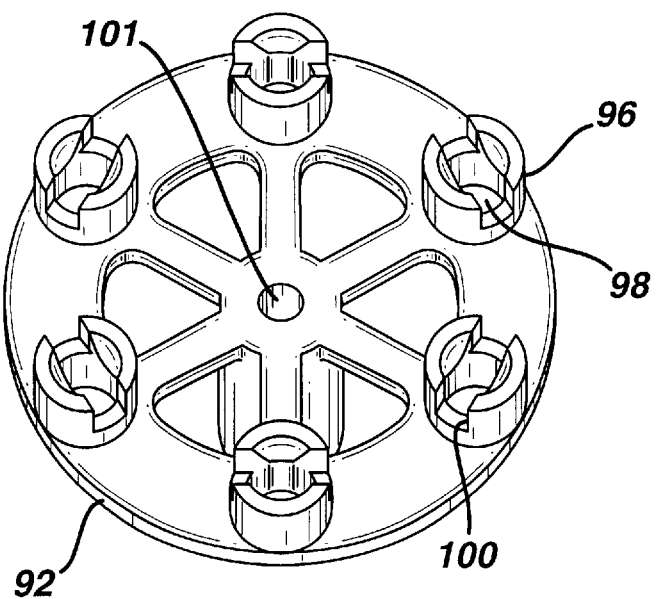
FIG. 10 is a perspective view of the device of FIG. 7.

FIGS. 9 and 10 show perspective views of the device of FIGS. 7 and 8. Guide channel 98, with diameter at least as large as the outermost diameter of ledge 90 of post 88, is located in axial alignment with post guide 96 and passes through base platform 92 and partially through post guide 96. The upper portion of post guide 96 is designed to be radially flexible by way of perforations 100 which allow the upper portion of post guide 96 to bend outwards to receive ledge 90 of post 88 of upper component 82.

Figure 11:
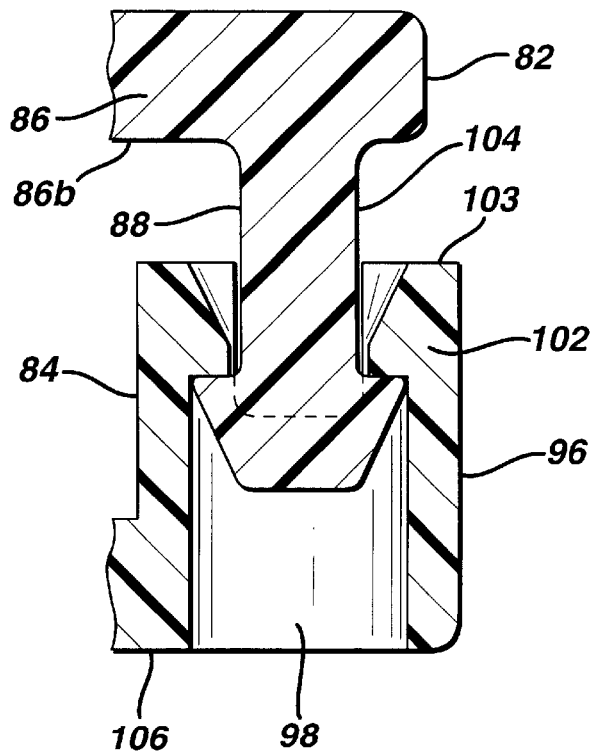
FIG. 11 is a cross-sectional side view of a two-piece device of the present invention when there is no axial load on the device and the gap is completely open.

The method of connection between upper component 82 and base component 84 is shown in FIG. 11. FIG. 11 is a cross-sectional side view of the device of FIGS. 7 through 10. Upper component 82 and base component 84 are connected together by mechanical fastening between posts 88 and post guides 96 by way of ledge 90 on each post 88 locking with latch 102 on each post guide 96. As upper component 82 and base component 84 are pressed together with the axis of each post 88 aligned with the axis of each post guide 96, each post guide 96 is forced to expand outward around ledge 90 of each post 88 until ledge 90 passes latch 102, at which point the post guide 96 returns to its unloaded configuration so that latch 102 captures ledge 90. Once upper component 82 and base is component 84 are connected together, they can not be easily separated. Preferably the geometry of ledge 90 and post guide 96 is such that the elastic limit of post guide 96 would not be exceeded during connection of upper component 82 and base component 84.

Figure 12:
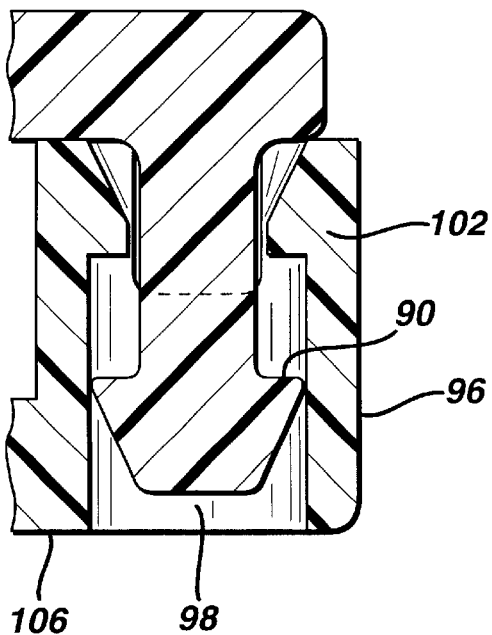
FIG. 12 is a cross-sectional side view of a portion of a two-piece device of the present invention when there is axial load on the device such that the gap is closed.

Once upper component 82 and base component 84 are connected together, they are free to move with respect to each other through CDD 104 between upper surface 103 of guide posts 96 of base component 84 and lower surface 86b of load support 86 of upper component 82. CDD 104 between the assembled parts provides a minimum amount of scaffold deformation effective to stimulate cell activity and matrix synthesis, i.e. tissue growth, and a maximum amount of scaffold deformation effective to prevent substantial damage to the scaffold or to the cells and the healing tissue. While the relative travel between upper component 82 and base component 84 is less than CDD 104, the applied load is borne entirely by the scaffold. When CDD 104 is closed and load platform 86 comes in contact with post guides 96, as shown in FIG. 12, the stiffness of the device is much higher than the stiffness of the scaffold, since post guides 96 would then act as load-bearing columns to protect the scaffold from high displacement and load. Preferably the lengths of posts 88 are such that they will not protrude beyond bottom surface 106 of base component 84 in the closed configuration shown in FIG. 12. Once posts 88 are aligned within guide channels 98 in guide posts 96, resistance to rotation of upper component 82 relative to base component 84 is provided. Clearance between ledges 90 of posts 88 and guide channels 98 of post guides 96 allows upper component 82 to displace freely towards base component 84.

Figure 13:
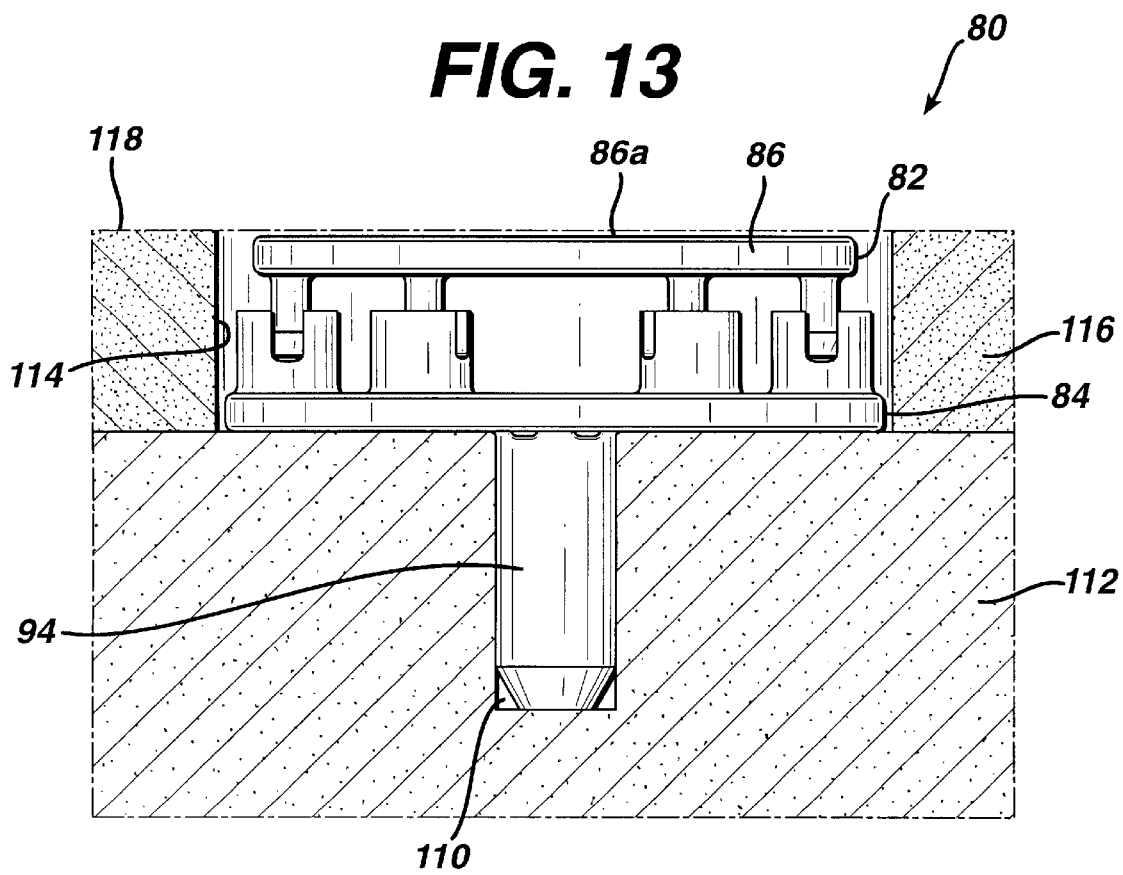
FIG. 13 is a side elevation view of the device of FIG. 8 as deployed in bone.

FIG. 13 shows a side elevation view of the surgical placement of scaffold fixation device 80. Bone hole 110 is drilled in bone tissue 112 to a diameter such that an interference fit is made between bone hole 110 and anchoring section 94. Cartilage hole 114 is drilled in cartilage tissue 116 to a diameter at least as large as the outermost diameter of load support 86. The depth of bone hole 110 is drilled such that when fixation post 94 is inserted completely into hole 110 upper surface 86a of load support 86 preferably lies in alignment with or slightly below upper cartilage surface 118 of adjacent cartilage tissue 116 when no vertical load is applied to the device. The scaffold resides in the available space between upper component 82 and base component 84 and fills the diameter of cartilage hole 114. Fixation post 94 also may include ribs, serrations, or other surface roughness or bone engagement features that improve the attachment of the post to the surrounding bone and/or to prevent rotation of the device and scaffold once implanted. Fixation device 80 also may comprise guide wire channel 101 passing completely through upper component 82 and base component 84. A surgical guide wire may be passed through guide wire channel 101 during surgery to align base component 84 and upper component 82 with bone hole 110 and cartilage hole 114. FIGS. 7 through 12 show an embodiment of the invention having six sets of posts 88 and post guides 96. At least 3 sets of posts 88 and post guides 96 are preferred for mechanical stability.

Figure 14:
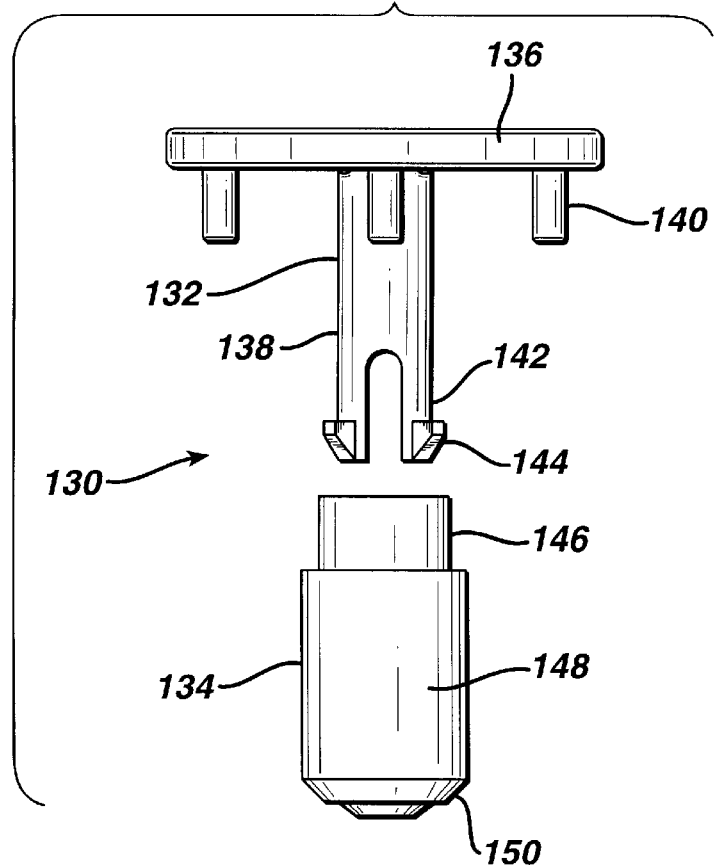
FIG. 14 is a side elevation view of a two-piece device of the present invention.
Figure 15:
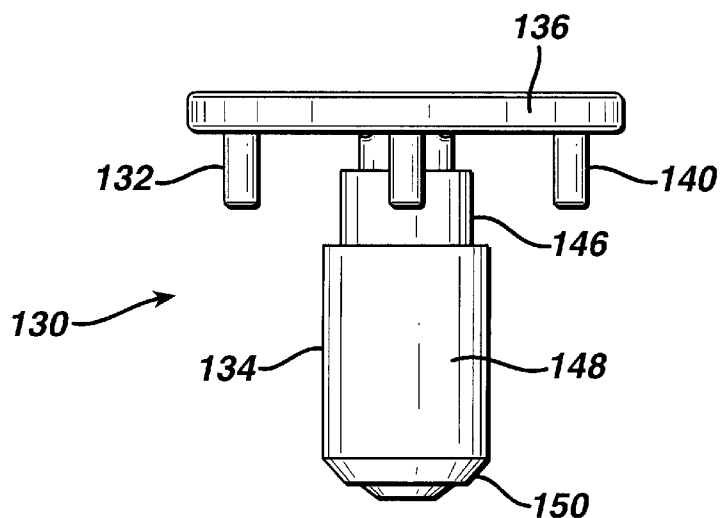
FIG. 15 is a side elevation view of the device of FIG. 14 after connection of the pieces.
Figure 16:
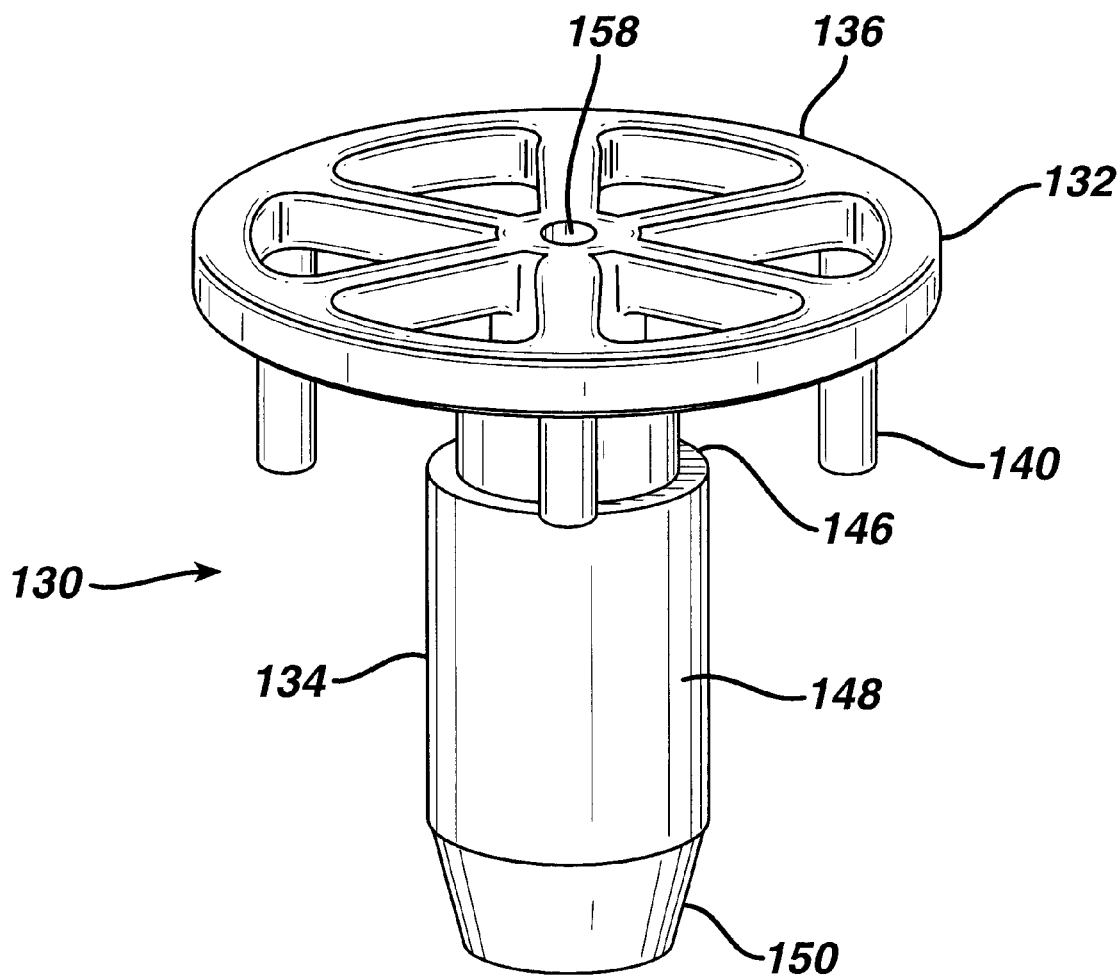
FIG. 16 is a perspective view of the device of FIG. 15.

Another embodiment of the present invention is shown in FIGS. 14 through 20. FIG. 14 shows a side view of unassembled scaffold fixation device 130 that comprises top component 132 and fixation component 134. Top component 132 comprises load support 136 and connecting post 138. Top component 132 also may include support columns 140 protruding downward from load platform 136. Connecting post 138 includes radially flexible members 142 with latches 144 for connection to fixation component 134. Fixation component 134 comprises shoulder 146, anchor section 148, and also may comprise chamfer 150 on the lower tip of anchor section 148 to help align fixation component 134 during insertion into a hole in bone. FIG. 15 shows a side view of scaffold fixation device 130 after connection of top component 132 and fixation component 134. FIG. 16 shows a perspective view of scaffold fixation device 130.

Figure 17:
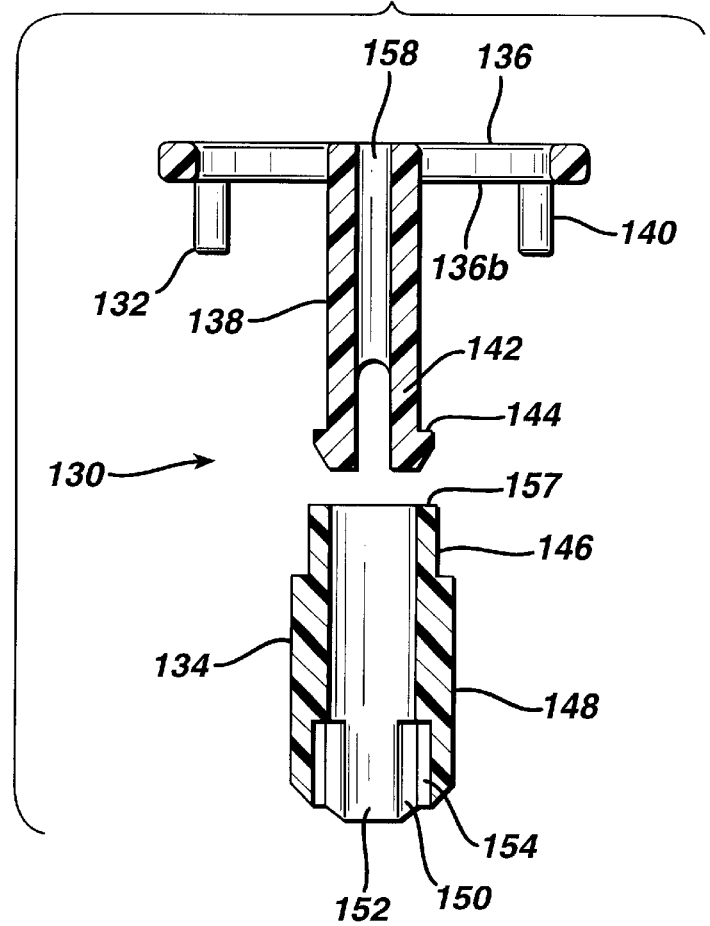
FIG. 17 is a cross-sectional side view of the device of FIG. 14.
Figure 18:
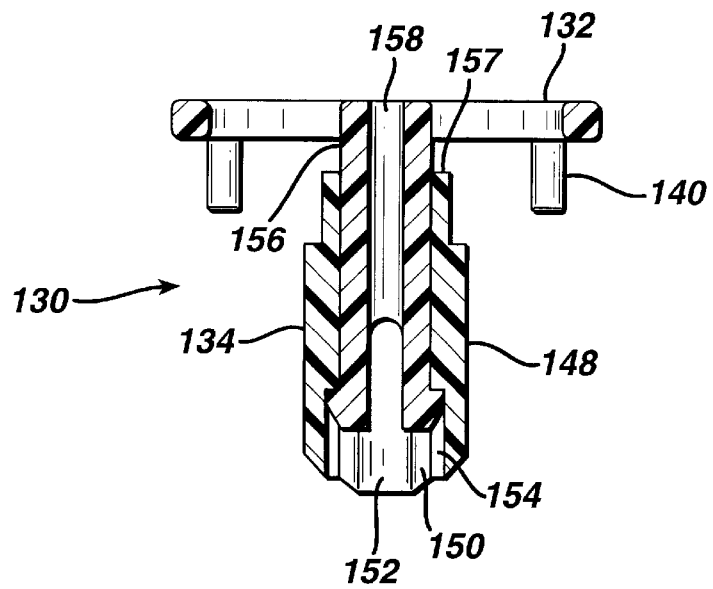
FIG. 18 is a cross-sectional side view of the device of FIG. 15 after connection of the pieces.
Figure 19:
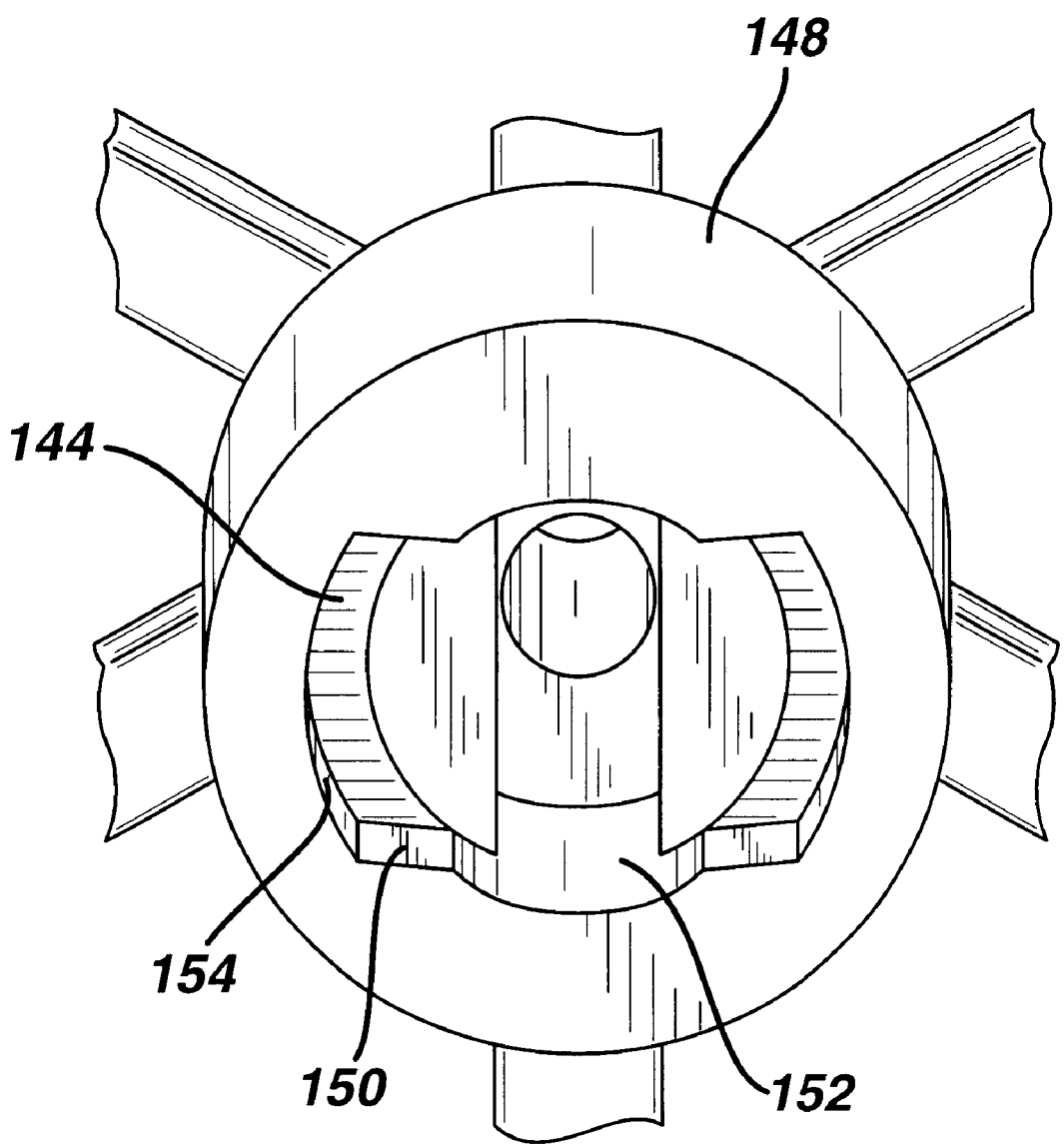
FIG. 19 is a perspective view of a portion of another two-piece alternative embodiment of the present invention.

As shown in FIGS. 17 and 18, cross-sectional side views of the fixation device described in FIGS. 14, 15 and 16, fixation component 134 also comprises post channel 152 passing longitudinally therethrough and latch channels 154, which pass partially through fixation component 134 from the bottom end. Post channel 154 has a diameter that is at least as large as the diameter of connecting post 138 and latch channels 154 have the same general shape as latches 144, with at least the same dimensions so that latches 144 fit in latch channels 154 without interference. The shape of latches 144 and latch channels 154 is such that there are flat surfaces 150 in latch channels 154 that interact with mating surfaces on latches 144 of flexible members 142 to prevent rotation of top component 132 with respect to fixation component 134. FIG. 19 shows a perspective view of a portion of scaffold fixation assembly 130 showing the fit between latches 144 and latch channels 154.

Assembly of scaffold fixation device 130 is achieved by inserting connecting post 138 of top component 132 axially into post channel 152 in fixation component 134 with latches 144 in alignment with latch channels 154. Flexible members 142 will deflect to enter post channel 152 and will return to their unloaded configuration when top component 132 is displaced downwards until latches 144 travel beyond the upper surfaces of the latch channels. Preferably, the geometry of flexible members 142 and post channel 152 are such that the elastic limit of flexible members 142 will not be exceeded during connection of top component 132 to fixation component 134.

FIG. 18 is a cross-sectional side view of the device described in FIG. 17 after connection of the pieces. Once top component 132 and fixation component 134 are connected together, they are free to move with respect to each other through CDD 156 between upper surface 157 of shoulder 146 of fixation component 134 and lower surface 136b of load support 136 of top component 132. CDD 156 between the assembled parts provides a minimum amount of scaffold deformation effective to stimulate cell activity and matrix synthesis, and a maximum amount of scaffold deformation effective to prevent substantial damage to the scaffold and/or to the cells and the healing tissue. When the relative travel between top component 132 and base component 134 is less than CDD 156, the applied load is borne entirely by the scaffold. When CDD 156 is closed and load support 136 comes in contact with shoulder 146, the stiffness of the device is much higher than the stiffness of the scaffold, since shoulder 146 then acts as a load-bearing column to protect the scaffold from high displacement and load. Another or an additional structural support to protect the scaffold would be provided if support columns 140 of the load support 136 were also included in the invention. Preferably, the device will contain at least one of shoulder 146 or support columns 140.

Figure 20:
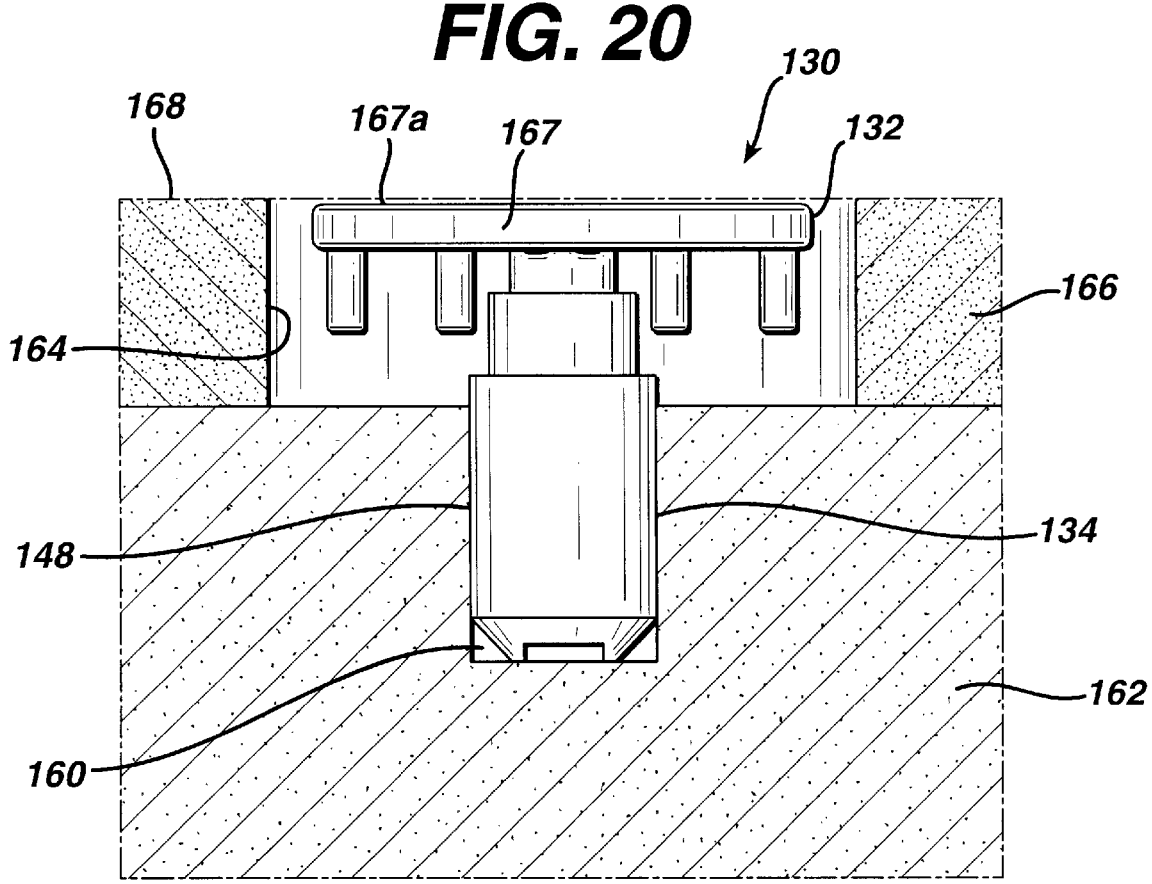
FIG. 20 is a side elevation view of the device of FIG. 19 as deployed in bone.

FIG. 20 shows a side elevation view of the surgical placement of scaffold fixation device 130. Bone hole 160 is drilled in bone tissue 162 to a diameter such that an interference fit is made between bone hole 160 and anchor section 148. Cartilage hole 164 is drilled in cartilage tissue 166 to a diameter at least as large as the outermost diameter of upper component 132. The depth of bone hole 160 is drilled such that when fixation component 134 is inserted completely into the hole, upper surface 167a of load support 167 preferably lies in alignment with or slightly below upper cartilage surface 168 of adjacent cartilage tissue 166 when no vertical load is applied to the device. The scaffold resides in the available space between top component 132 and bone tissue 162 and fills the diameter of cartilage hole 164. The fixation section 148 may also include ribs, serrations, or other surface roughness or bone engagement features that improve the attachment of the post to the surrounding bone and/or prevent rotation of the device and scaffold.

Figure 21:
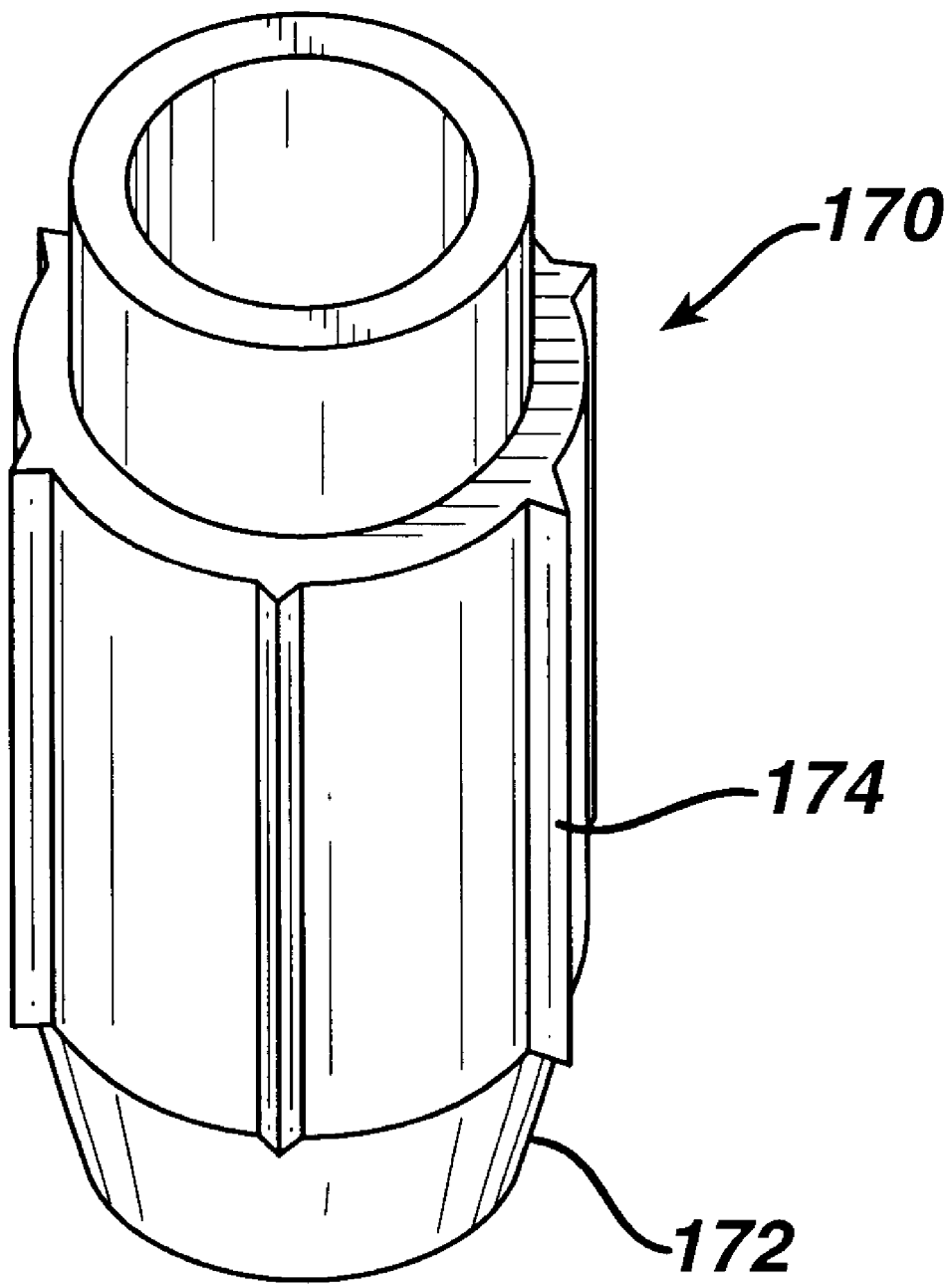
FIG. 21 is a perspective view of an anchoring section that comprises ribs for preventing rotation of the device.

FIG. 21 shows anchoring section 170 of the type disclosed in FIGS. 14–20, comprising chamfer 172 and ribs 174 for preventing rotation of the device once implanted.

Suitable materials from which the scaffold fixation device may be formed include biocompatible polymers selected from the group consisting of aliphatic polyesters, polyorthoesters, polyanhydrides, polycarbonates, polyurethanes, polyamides and polyalkylene oxides. The present invention also can be formed from absorbable glasses or ceramics comprising calcium phosphates and other biocompatible metal oxides (i.e., CaO). The present invention can also be formed from metals. The fastener of the present invention further can comprise combinations of metals, absorbable ceramics, glasses and polymers.

In the preferred embodiment, the scaffold fixation device comprises aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, -caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

I claim:

1. A scaffold fixation device suitable for use in articular cartilage repair, comprising:

means for anchoring said fixation device to bone, a load support comprising an upper surface and a lower surface; and means for providing deformation of said fixation device, wherein said deformation provides a controlled load on a scaffold provided with said fixation device, which controlled load is effective to stimulate growth of cells and synthesis of a cell matrix in and/or on said scaffold without substantially damaging said cells, cell matrix or scaffold.

2. The device of claim 1 wherein said means for providing deformation of said device comprises a flexible structural member.

3. The device of claim 2 wherein said flexible structural member folds, collapses or otherwise deforms in response to load applied to said load support.

4. The device of claim 1 wherein said fixation device comprises an upper component comprising said load support and posts protruding downward from said load support near an outer perimeter thereof; and a base component comprising a base platform and post guides protruding upward from said base platform near an outer perimeter thereof, said post guides being in axial alignment with said posts, wherein said upper component is free to deform with respect to said base component through a controlled deformation distance between an upper surface of said guide post and said lower surface of said load support, and wherein said means for providing deformation comprises said post and post guide.

5. The device of claim 1 further comprising means for substantially preventing rotation of said device and said scaffold.

* * * * *